(12) United States Patent
Chang et al.

(10) Patent No.: US 8,513,015 B2
(45) Date of Patent: Aug. 20, 2013

(54) LAMININ-ENTACTIN COMPLEX AND CELL CULTURE ARTICLE AND METHODS THEREOF

(75) Inventors: Theresa Chang, Painted Post, NY (US); Jin Liu, Painted Post, NY (US); Odessa Natalie Petzold, Elmira, NY (US); Ruchirej Yongsunthon, Painted Post, NY (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 13/111,234

(22) Filed: May 19, 2011

(65) Prior Publication Data

US 2011/0306136 A1      Dec. 15, 2011

Related U.S. Application Data

(60) Provisional application No. 61/353,883, filed on Jun. 11, 2010.

(51) Int. Cl.
*C12N 5/00* (2006.01)

(52) U.S. Cl.
USPC .......................................... 435/402; 435/395

(58) Field of Classification Search
USPC .................................. 435/402, 395
See application file for complete search history.

(56) References Cited

U.S. PATENT DOCUMENTS

| | | | | |
|---|---|---|---|---|
| 4,839,292 A * | 6/1989 | Cremonese | ................. | 435/297.2 |
| 7,371,400 B2 | 5/2008 | Borenstein et al. | ............ | 424/423 |
| 7,378,507 B2 | 5/2008 | Ferrara et al. | ................. | 530/399 |
| 7,384,786 B2 | 6/2008 | Freyman et al. | ............... | 435/395 |
| 7,390,879 B2 | 6/2008 | Ashkenazi et al. | ............ | 530/350 |
| 7,399,634 B2 | 7/2008 | Mochitate | ....................... | 435/395 |
| 7,410,798 B2 | 8/2008 | Mandalam et al. | ........... | 435/366 |
| 7,449,333 B2 | 11/2008 | Rolland et al. | ................. | 435/325 |
| 7,455,983 B2 | 11/2008 | Xu et al. | ....................... | 435/7.21 |
| 7,507,581 B2 | 3/2009 | Navran, Jr. | ..................... | 435/391 |
| 7,531,354 B2 | 5/2009 | Stice et al. | ..................... | 435/325 |
| 7,541,187 B2 | 6/2009 | Myles et al. | ................... | 435/395 |
| 7,560,281 B2 | 7/2009 | Carpenter et al. | ............. | 435/377 |
| 7,579,189 B2 | 8/2009 | Freyman et al. | ............... | 435/395 |
| 7,592,175 B2 | 9/2009 | Amit et al. | ...................... | 435/373 |
| 7,604,929 B2 | 10/2009 | Dryden et al. | .................. | 435/1.1 |
| 7,608,455 B2 | 10/2009 | Wu et al. | ....................... | 435/402 |

OTHER PUBLICATIONS

Caron et al. (Induction of Albumin Gene Transcription in Hepatocytes by Extracellular Matrix Proteins. Molecular and Cellular Biology. 1990, 10(3):1239-1243).*
BD Biosciences, Material Data Sheet, Catalog No. 354259, Lot No. A6683, Laminin/Entactin, High Concentration, 10.5 mg, www.bdbiosciences.com, Mar. 3, 2010, 4 pages.
BD Biosciences, Material Data Sheet, Catalog Number 354259, Lot Number 75447, Laminin—Ultrapure, Mouse, www.bdbiosciences.com, Mar. 3, 2010, 2 pages.

* cited by examiner

*Primary Examiner* — Karen Cochrane Carlson
*Assistant Examiner* — Natalie Moss
(74) *Attorney, Agent, or Firm* — John L. Haack

(57) ABSTRACT

A cell culture system including: a substrate, a substrate coating, one or more live cells, and an overlay source. The substrate coating and overlay can be laminin, and laminin•entactin complex, respectively. Alternatively, the substrate coating and overlay can be laminin•entactin complex, and laminin, respectively. The cell culture system can further include liquid media and a protective cover. A method for making and using the system in cell culture articles and culture methods, as defined herein, is also disclosed.

17 Claims, 5 Drawing Sheets

LAMININ-ENTACTIN COMPLEX AND CELL CULTURE ARTICLE AND METHODS THEREOF

CROSS-REFERENCE TO RELATED APPLICATION

This application claims the benefit of priority under 35 U.S.C. §119 of U.S. Provisional Application Ser. No. 61/353,883, filed on Jun. 11, 2010, the content of which is relied upon and incorporated herein by reference in its entirety.

The entire disclosure of any publication, patent, or patent document mentioned herein is incorporated by reference.

BACKGROUND

The disclosure relates generally to a cell culture composition, a cell culture additive (i.e., an overlay or overlay source), and methods of making and using the composition and additive.

SUMMARY

The disclosure provides a mammalian cell culture composition comprising a laminin and entactin complex, a cell culture liquid media additive (i.e., an overlay or overlay source), a cell culture article incorporating the complex, and a method of making and using the article.

BRIEF DESCRIPTION OF THE DRAWINGS

In embodiments of the disclosure.

DETAILED DESCRIPTION

Figure 1:
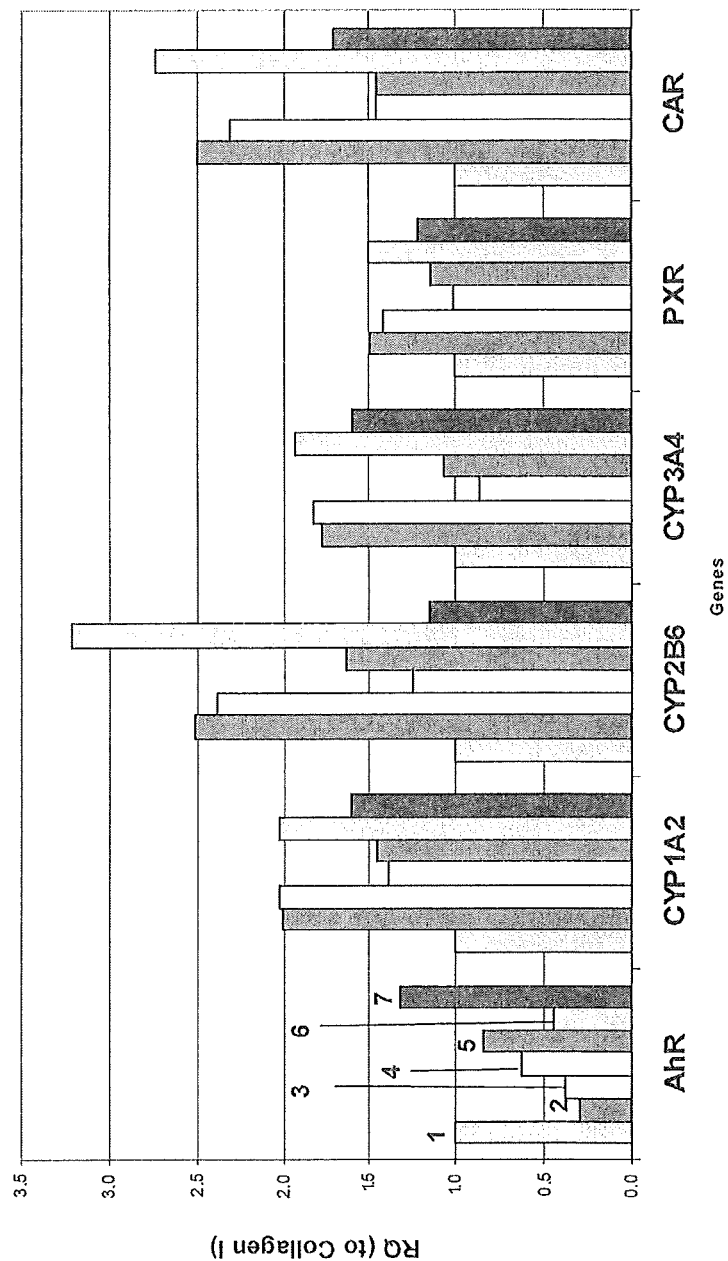
FIG. 1 shows a chart of relative quantitation (RQ) for selected components present in and isolated from Matrigel as cell culture overlays (OL) and their comparative effect on gene expression.

Various embodiments of the disclosure will be described in detail with reference to drawings, if any. Reference to various embodiments does not limit the scope of the invention, which is limited only by the scope of the claims attached hereto. Additionally, any examples set forth in this specification are not limiting and merely set forth some of the many possible embodiments of the claimed invention.

DEFINITIONS

"Overlay" or like terms refer to a relatively thin continuous or substantially continuous film, or substantive layer, having a thickness, for example, of about 200 nm to about 20 micrometers, of about 1 to about 10 micrometers, and like thicknesses, including intermediate values and ranges, atop a cell culture layer on a coated or uncoated substrate. An overlay can be visible to an observer and can be formed from deposition of source ingredients that may be contained in the surrounding liquid media (overlay source). An overlay can be sourced or generated, for example, by deposition (e.g., gelation, agglomeration, precipitation, and like processes) from source materials dissolved or suspended, for example, at about 0.25 to about 5 mg per mL, 1.5 to about 1 mg per mL, and like concentrations, including intermediate values and ranges, in the liquid media surrounding the cell layer.

"Sandwich" or like terms refer to a known cell culture article having a coated substrate, a cell layer, and a relatively thick gel layer having a thickness of about 0.5 to about 2 millimeters atop the cell layer.

"Roughness," "$R_q$," or like terms refer a well understood and widely recognized parameter that uses atomic force microscopy (AFM) to describe surface topography. By definition, much of the surface detail is averaged out by image processing to a single final roughness value $R_q$ give by:

$$R_q = \sqrt{\frac{1}{n}\sum_{i=1}^{n}(z_j - \bar{z})^2}$$

where n is the total number of pixels (i from 1 to n) in an image and z is the height value. Despite the loss of information incurred by collapsing an entire image to a single numerical value, a desirable aspect of the roughness metric is that it can identify significant changes in topography.

"RQ," or "relative quantitation" or like terms refer to all the disclosed gene expression results, which are normalized or relative to the collagen-I result of 1.

"Laminin•entactin complex" or like terms refer to an approximate 1:1 mole ratio of the bound product of a mixture of laminin and entactin.

"MFE" refers to an abbreviation for Multifunctional Enhancement (MFE™) plating media available from Multi-Cell Technologies, Inc., (www.multicelltech.com).

"ECM" refers to an abbreviation for extracellular matrix.

"Include," "includes," or like terms means encompassing but not limited to, that is, inclusive and not exclusive.

"About" modifying, for example, the quantity of an ingredient in a composition, concentrations, volumes, process temperature, process time, yields, flow rates, pressures, and like values, and ranges thereof, employed in describing the embodiments of the disclosure, refers to variation in the numerical quantity that can occur, for example: through typical measuring and handling procedures used for making compounds, compositions, composites, concentrates or use formulations; through inadvertent error in these procedures; through differences in the manufacture, source, or purity of starting materials or ingredients used to carry out the methods; and like considerations. The term "about" also encompasses amounts that differ due to aging of a composition or formulation with a particular initial concentration or mixture, and amounts that differ due to mixing or processing a composition or formulation with a particular initial concentration or mixture. The claims appended hereto include equivalents of these "about" quantities.

"Consisting essentially of" in embodiments refers, for example: to a cell culture system including: a substrate coating including a laminin•entactin complex and the overlay source including laminin, or alternatively, a substrate coating including laminin and the overlay source including the laminin•entactin complex; to a method of making the cell culture system, or cell culture system formulation, and articles, devices, or any apparatus of the disclosure, and can include the components or steps listed in the claim, plus other components or steps that do not materially affect the basic and novel properties of the compositions, articles, apparatus, or methods of making and use of the disclosure, such as particular reactants, particular additives or ingredients, a particular agents, a particular surface modifier or condition, or like structure, material, or process variable selected. Items that may materially affect the basic properties of the components or steps of the disclosure or that may impart undesirable characteristics to the present disclosure include, for example, cell culture compositions, cell culture articles, and like implementations which do not have the structure, properties, and advantages, as disclosed herein.

The indefinite article "a" or "an" and its corresponding definite article "the" as used herein means at least one, or one or more, unless specified otherwise.

Abbreviations, which are well known to one of ordinary skill in the art, may be used (e.g., "h" or "hr" for hour or hours, "g" or "gm" for gram(s), "mL" for milliliters, and "rt" for room temperature, "nm" for nanometers, and like abbreviations).

Specific and preferred values disclosed for components, ingredients, additives, and like aspects, and ranges thereof, are for illustration only; they do not exclude other defined values or other values within defined ranges. The compositions, apparatus, and methods of the disclosure can include any value or any combination of the values, specific values, more specific values, and preferred values described herein.

The disclosure relates to a mammalian cell culture media additive (i.e., an overlay), which additive promotes cell function that more closely resembles in vivo cell conditions compared to, for example, tissue culture treated (TCT) or CellBIND™ treated polystyrene surfaces. In particular, the in vitro culture of hepatocytes (liver cells) is important in drug discovery processes, for example, predictive ADMETox (see for example, Kleinman, H. K., et al., Isolation and characterization of type IV procollagen, laminin, and heparin sulfate proteoglycan from the EHS sarcoma, *Biochemistry*, 21:6188 (1982)), since drugs or drug byproducts can often be more toxic after metabolism by the Cytochrome P450 (CYP450) enzyme in the liver than prior to the detoxification process. An activated metabolic intermediate can interact with other compounds (e.g., other drugs), cause oxidative damage to surrounding tissue, or both. However, primary hepatocyte cells in vitro can quickly lose function before the introduction of the drug, including albumin production and CYP450 activity, which activities can control the cell's ability to metabolize drug molecules. Toxicity and drug interaction studies with these compromised cells are, therefore, less informative.

State-of-the-art culturing materials for hepatocyte culture and assay are, according to literature sources, Matrigel™ overlay with collagen-I as the substrate coating. Both are animal derived. Hepatocytes cultured on Matrigel™ (specifically formulated for hepatocytes) form spheroid aggregates and show enhanced function. Hepatocytes cultured on collagen are flat and spread, which is advantageous for proliferation, but not particularly ideal for function. If the hepatocytes are sandwiched between two layers of collagen (a "collagen sandwich"), the cells adopt a polygonal appearance and show some enhancement in function, particularly transport function, albeit not to the same extent as Matrigel™. However, primary hepatocytes cultured on collagen may not function well, and primary hepatocytes cultured on Matrigel™ appear as clusters of cells, which may be problematic for assay development and interpretation.

One established method to achieve enhanced function of primary hepatocytes is by culturing with a Matrigel™ overlay, that is, a small amount, such as 0.25 mg of Matrigel/mL of media, is added into the liquid media formulation. However, the inherent problems with Matrigel™, such as the high lot-to-lot variability and possible interactions with one or more components of Matrigel™ can be problematic for predictive toxicity since Matrigel™ is composed of a myriad of biologically active components that have not been fully identified and may be present in undefined and variable quantities.

BD Matrigel™ Matrix (see Kleinman, *Biochemistry*, supra.), is a reconstituted basement membrane extracted from Engelbreth-Holm-Swarm (EHS) mouse sarcoma, a tumor that is rich in ECM proteins. Its major component is laminin, followed by collagen-IV, heparin sulfate proteoglycan, and entactin. Entactin, also known as nidogen, is an invariant component of basement membranes. It is known mostly as a linker protein that plays a role in the assembly of basement membrane components. Entactin forms a strong 1 to 1 complex with laminin and has been demonstrated to bind to other ECM biomolecules such as collagen-V, perlecan, and binding to the $\alpha 3\beta 1$ (alpha3beta1) integrin via a calcium ion mediated interaction. The entactin and laminin complex is also a known ligand for the leukocyte antigen-related protein (LAR) a family of phosphatases, and is known to regulate cell adhesion and morphology.

In embodiments, the disclosure provides a cell culture system comprising:
  a substrate;
  a coating on the substrate;
  one or more live cells on the coated substrate; and
  an overlay source,
  i. when the substrate coating comprises a laminin•entactin complex, the overlay source comprises laminin, or
  ii. when the substrate coating comprises laminin, the overlay source comprises the laminin•entactin complex.

In embodiments, the system can further comprise, for example, a liquid media, a cover, and combinations thereof. The liquid media can be, for example, an overlay source comprising laminin or a laminin•entactin complex, and serum free media. The cover can be, for example, a removable, gas permeable, liquid leak-proof seal. The live cells can be, for example, hepatocyctes, primary hepatocytes, mammalian hepatic cell lines, stem cells, and like cell lines, or combinations thereof. The laminin•entactin complex can be, for example, laminin and entactin molecularly associated in a relative mole ratio of 1:1. The laminin can be, for example, murine sourced and the entactin can be, for example, human sourced. The laminin•entactin complex can be, for example, the laminin and the entactin molecularly associated in a relative weight ratio of about 5:1 to about 9:1, in a relative weight ratio of about 6:1 to about 8:1, and in a relative weight ratio of about 6.5:1 to about 7.5:1, including intermediate values and ranges.

In embodiments, the laminin•entactin complex can be present in the substrate coating, for example, in an amount of from about 10 to about 100% by weight, and the laminin can be present in the overlay source, for example, in an amount of from about 5 to about 20% by weight, and in an amount of from about 10 to about 100% by weight (i.e., 1 micrograms/$cm^2$ to 20 micrograms/$cm^2$ of surface area) (greater than about 100 nm in thickness), and the laminin can be present in the overlay source in an amount of from about 5 to about 20% by weight (0.25 milligrams/mL to 1 milligrams/mL).

In embodiments, the laminin can be, for example, present in the substrate coating, for example, in an amount of from about 10 to about 100% by weight (e.g., 1 micrograms/cm$^2$ to 20 micrograms/cm$^2$ of surface area), and the laminin•entactin complex can be present in the overlay source in an amount of, for example, from about 5 to about 20% by weight (e.g., 0.25 milligrams/mL to 1 milligrams/mL).

In embodiments, the laminin•entactin complex and the laminin can be, for example, essentially free of endogenous growth stimulants, proteolytic enzymes, or combinations thereof.

The substrate can be, for example, a petri dish, a cell culture flask, a multi-well plate, a non-porous slide, a porous slide, a chamber/multi-chamber slide, a cell culture device, a microcarrier, and like surfaces or containers, or combinations thereof.

In embodiments, the disclosure provides a method of making a cell culture article including:

coating a substrate with a laminin•entactin complex or laminin;

contacting the coated substrate with live cells to form at least a monolayer of the live cells on the coated substrate; and providing an overlay source comprising laminin when the substrate is coated with the laminin•entactin complex, or providing an overlay source comprising the laminin•entactin complex when the substrate is coated with the laminin, to form an overlay on the live cells on the coated substrate.

In embodiments, the cell culture preparative method can further comprise, for example, removing the overlay source from the article. Additionally or alternatively, the method can further comprise adding a liquid media to the article.

In embodiments, the disclosure provides a method of culturing cells comprising:

providing a cell culture system comprising:
 i. a substrate;
 ii. a coating on the substrate;
 iii. one or more live cells on the coated substrate; and
 iv. an overlay source, where if the substrate coating comprises a laminin•entactin complex then the overlay source comprises laminin, or if the substrate coating comprises laminin then the overlay source comprises the laminin•entactin complex; and optionally providing a user selected media to the article. The user selected media can be, for example, serum free.

In embodiments, the disclosure provides the aforementioned cell culture article where if the substrate coating is a laminin•entactin complex then the overlay source is laminin. In embodiments, the disclosure provides the aforementioned cell culture article where if the substrate coating is laminin then the overlay source is the laminin•entactin complex.

In embodiments, the disclosure provides a cell culture article comprising:

a substrate;
a laminin•entactin complex layer on the substrate;
a cell layer on the complex layer; and
a laminin overlay on the cell layer.

In embodiments, the disclosure provides a cell culture article comprising:

a substrate;
a laminin layer on the substrate;
a cell layer on the laminin layer; and
a laminin•entactin complex overlay on the cell layer.

In embodiments, the disclosure provides an article prepared by any of the preparative processes disclosed herein.

In embodiments, the disclosure provides an overlay composition. The disclosed overlay can eliminate the high variability and the potential for false readings that may be encountered with Matrigel or like products. The disclosed composition and method can eliminate many possible adverse interactions from the multitude of Matrigel components with the assay.

In embodiments, the disclosure provides a laminin and entactin complex for use in cell culture as a media additive for the restoration of membrane polarity and ultimately cellular function (i.e., detoxification) in hepatocytes. The disclosed laminin and entactin complex is an alternative to the Matrigel™ overlay (OL). While the laminin and entactin complex is present in Matrigel, among a myriad of other Engelbreth-Hole-Swarm (EHS) sarcoma components, the disclosed isolated and purified laminin and entactin complex exhibits cell culture performance as a media additive overlay that is comparable to Matrigel™. The purity of the disclosed laminin and entactin complex (e.g., greater than about 75%, about 85%, about 95%, about 99%, or above, including intermediate values and ranges) and simplified composition can, for example, reduce the variability in performance of the overlay, enhance the cellular function, and eliminate the potential for assay variability introduced by the compositional variability of Matrigel™. Furthermore, the disclosed laminin and entactin complex, when used in conjunction with a surface coating and as an overlay resulted in a well defined composition having excellent cellular function (as determined by gene expression and MRP2 staining shows bile canicular formation), that is comparable to spheroidal Matrigel™ culture. The branch-like bile canicular staining in the culture with overlay was similar to what is seen in Matrigel culture. Generally, the greater the observed canicular structure the greater the cell function since cell polarity is proportional to cell function (images not shown). Table 2 below summarizes the observed (image analysis) differences in canicular structure.

In embodiments, the disclosure provides methods of use of a laminin•entactin complex in cell culture media overlay, for example, which is comparable to a Matrigel™ overlay, for applications such as the restoration of membrane polarity and cellular function in primary human hepatocytes. The inherent high variability of a complex, multi-component material, such as Matrigel™, is a concern, particularly, for comparison of screening data between different experiments, especially across different Matrigel lots. It has been found that use of the laminin and entactin complex (an isolated component of Matrigel™) provides the same performance of the more complex mixture, but minimizes the potential for variability and false or erroneous readings attributable to, for example, the interference of one of the many biologically active molecules found in Matrigel™ with assay reagents and the detection readout. Furthermore, use of laminin as an overlay in conjunction with use of laminin•entactin complex as the surface coating, or alternatively, use of laminin•entactin complex as an overlay in conjunction with use of laminin as the surface coating, resulted in further enhancement in cell function. Many of the selected genes exhibited expression while others did not. For example, the CYP results indicated that the laminin•entactin complex overlay was comparable to the Matrigel overlay which was comparable to the combination of collagen-I and laminin•entactin complex overlay, whereas the laminin•entactin complex overlay had higher gene expression compared to no overlay present or other combinations as the overlay.

In embodiments, the disclosure provides particularly useful aspects, including for example: a well defined surface coating composition comprising laminin, and an overlay source comprising a laminin•entactin complex media additive, compared to the complex mixture known as Matrigel™, and the disclosed composition has only limited composition and performance variability compared to Matrigel™.

EXAMPLES

The following examples serve to more fully describe the manner of using the above-described disclosure, and to further set forth the best modes contemplated for carrying out various aspects of the disclosure. It is understood that these examples do not limit the scope of this disclosure, but rather are presented for illustrative purposes. The working examples further describe how to prepare and use the cell culture compositions, media additive, and cell culture article of the disclosure.

FIG. 1 shows a chart of relative quantitation for selected components present in or isolated from Matrigel as cell culture overlays (OL) and their comparative effect on gene expression. In these experiments CYP function was examined. The combination of Collagen-IV with laminin•entactin complex performs as well as Matrigel, whereas the same laminin•entactin complex in the absence of collagen-IV, that is with only laminin•entactin complex as overlay on collagen-I coating, performs less well.

The reference numerals for each cluster of bars in the FIG. 1 chart represent, respectively: collagen-I (1), Matrigel overlay (OL) (2), a mixture of collagen-IV and laminin•entactin complex OL (3), a mixture of collagen-IV and laminin OL (4), collagen-IV OL (5), laminin•entactin complex OL (6), and laminin OL (7).

Figure 2:
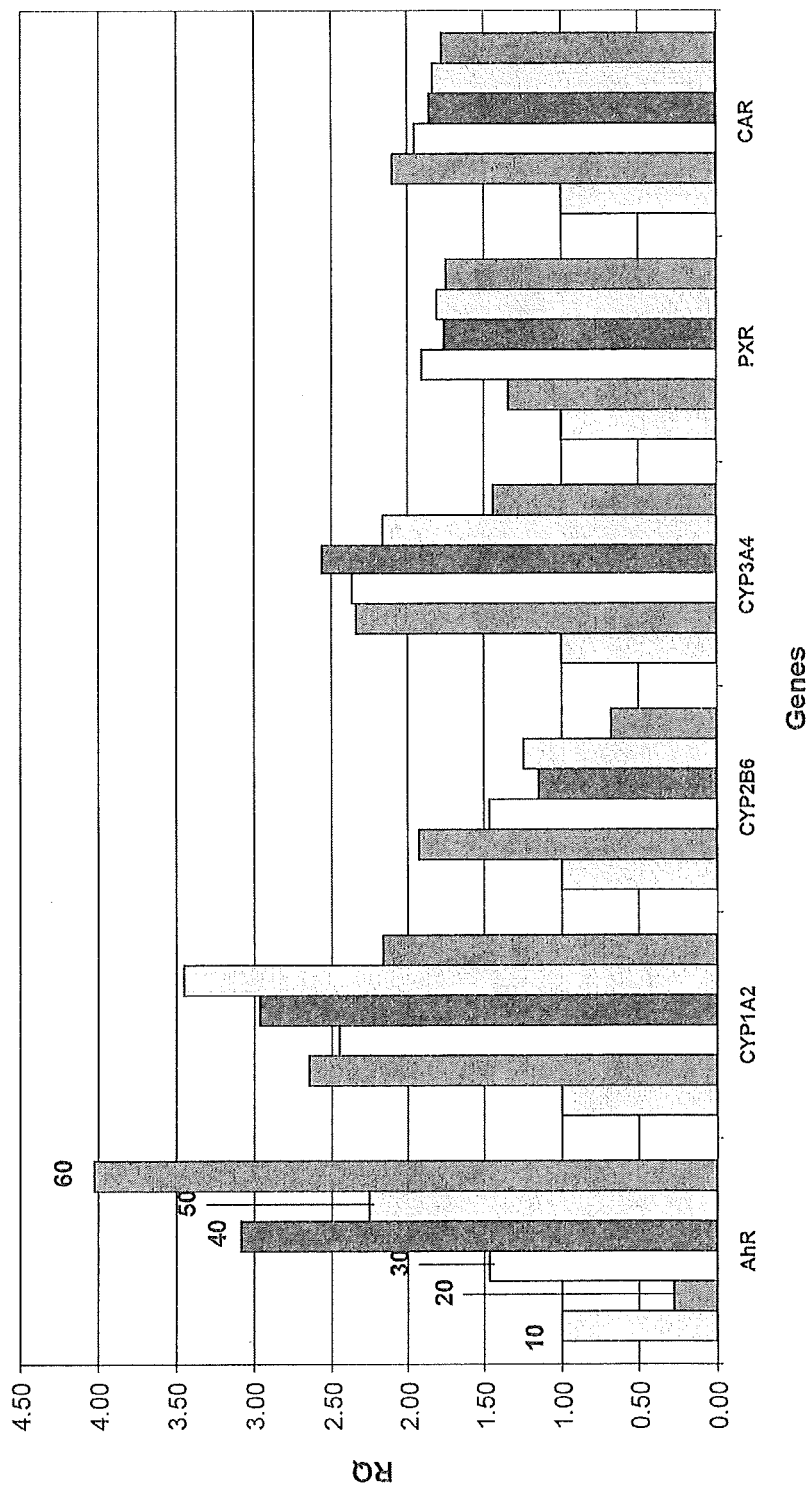
FIG. 2 shows a chart of relative quantitation for selected components present in and isolated from Matrigel and used as a cell culture substrate coating (OL) and their comparative effect on gene expression.

FIG. 2 shows a chart of relative quantitation for selected components present in or isolated from Matrigel as a cell culture substrate coating and their comparative effect on gene expression. The reference numerals for each cluster of bars in the FIG. 2 chart represent, respectively: collagen-I (10), BD laminin plate (20), BD laminin only coating (30), BD laminin•entactin complex coating (40), mouse laminin and human entactin coating mixture (50), and human laminin and human entactin coating mixture with no overlay (60). These experiments used Matrigel overlay and collagen-I coating combinations. It was found, for example, in Example 1 that the laminin•entactin complex is sufficient to replace the more complex mixture of Matrigel as an overlay. The coating composition can have an impact on gene expression of cytochromes (e.g., for detoxification). When Matrigel is selected as an overlay, there was little impact on the function, i.e., gene expression, based on the type of coating selected (e.g., surface coatings: collagen-I, collagen-IV, fibronectin, laminin, and Matrigel).

Figure 3:
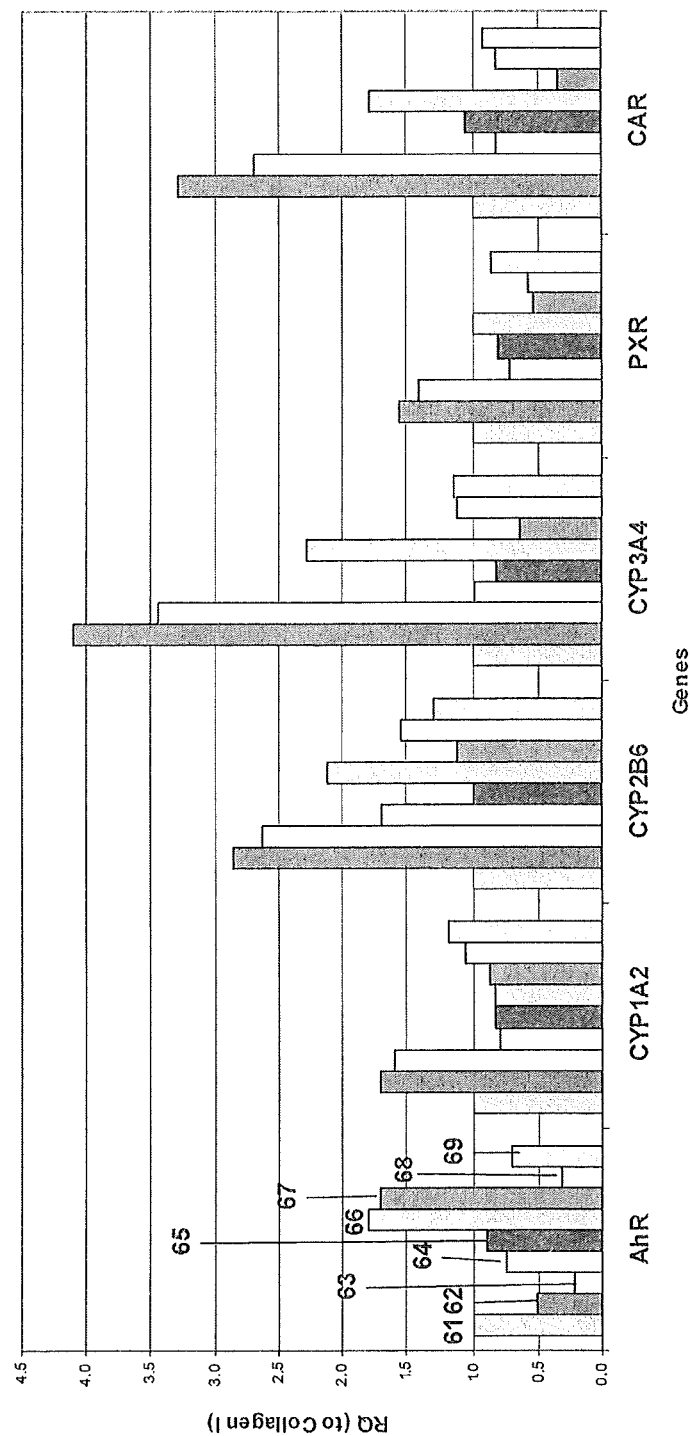
FIG. 3 shows a chart of relative quantitation for selected components present in and isolated from Matrigel and used as a cell culture overlay (OL) at selected concentrations, and their comparative effect on gene expression.

FIG. 3 shows a chart of selected components present in or isolated from Matrigel as a cell culture overlay (OL) at selected concentrations, and their comparative effect on gene expression. The reference numerals for each cluster of bars in the FIG. 3 chart represent, respectively: collagen-I only (61), BD Matrigel OL, 0.25 mg/mL (62), Matrigel OL, 0.5 mg/mL (63), laminin•entactin complex overlay, 0.16 mg/mL (64), laminin•entactin complex overlay, 0.21 mg/mL (65), laminin•entactin complex overlay, 0.25 mg/mL (66), entactin overlay, 0.25 mg/mL (67), entactin overlay, 0.125 mg/mL (68), and entactin overlay, 0.025 mg/mL (69). This set of experiments demonstrates that there is a dose response for a laminin•entactin complex overlay (i.e., increased dose provides a better response). Interestingly, there appears to be a negative correlation with entactin. That is, having an inverse dose dependence, where low concentrations of entactin are non-cytotoxic and possibly beneficial for gene expression, whereas higher doses of entactin are cytotoxic.

Figure 4:
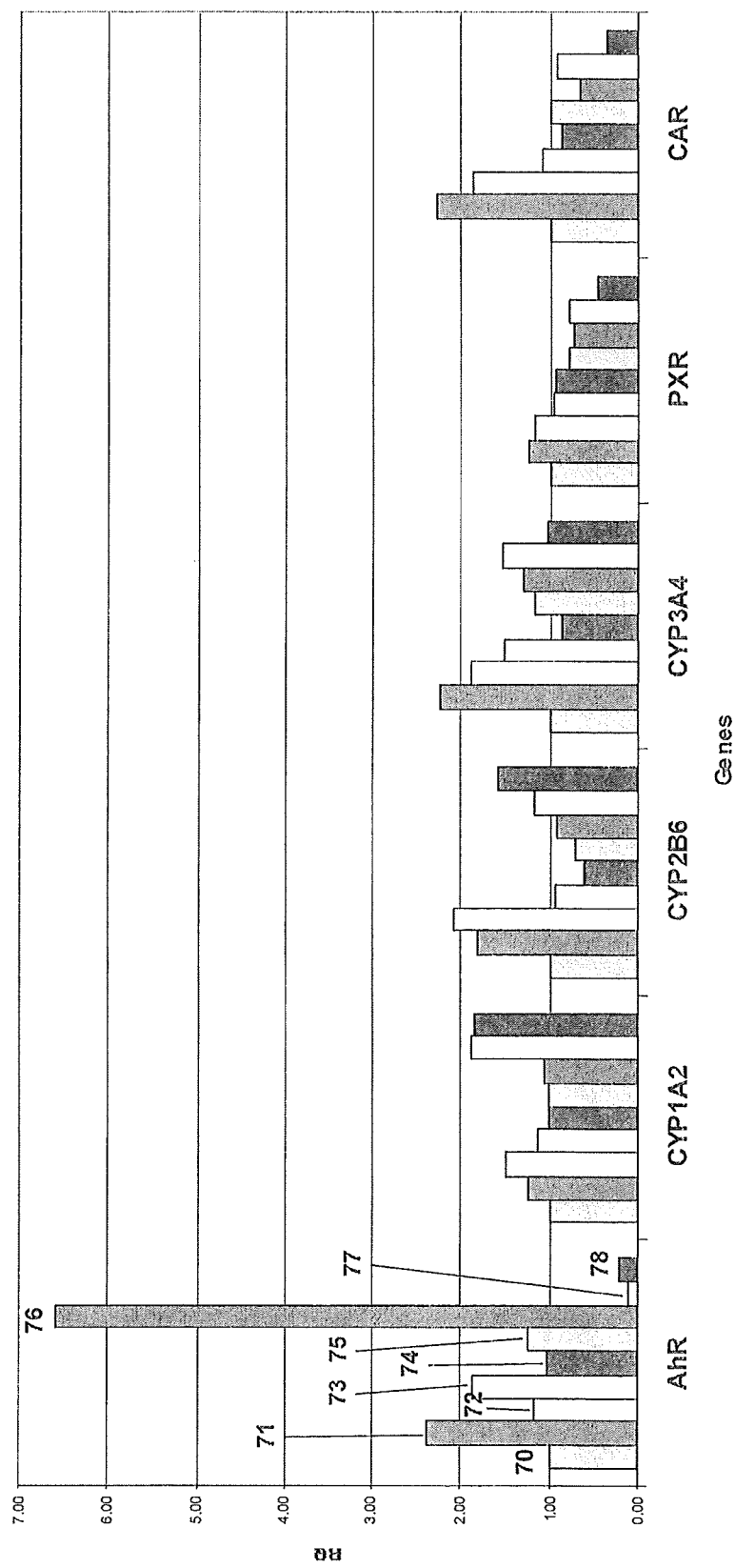
FIG. 4 shows a chart of relative quantitation for selected components present in and isolated from Matrigel as a cell culture overlay (OL), and having selected concentrations of laminin and entactin, and their comparative effect on gene expression.

FIG. 4 shows a chart of selected components present in or isolated from Matrigel as a cell culture overlay (OL), and having selected concentrations of laminin and entactin, and their comparative effect on gene expression. The reference numerals for each cluster of bars in the FIG. 4 chart represent, respectively: collagen-I overlay (70), Matrigel overlay, (71), BD laminin•entactin complex overlay (72), BD laminin only overlay (73), laminin•entactin complex (7:1=wt.:wt.) overlay (74), laminin entactin complex (3.5:1) overlay (75), laminin•entactin complex (1.75:1) overlay (76), laminin•entactin complex (1:1) overlay (77), and entactin only overlay (78).

Figure 5:
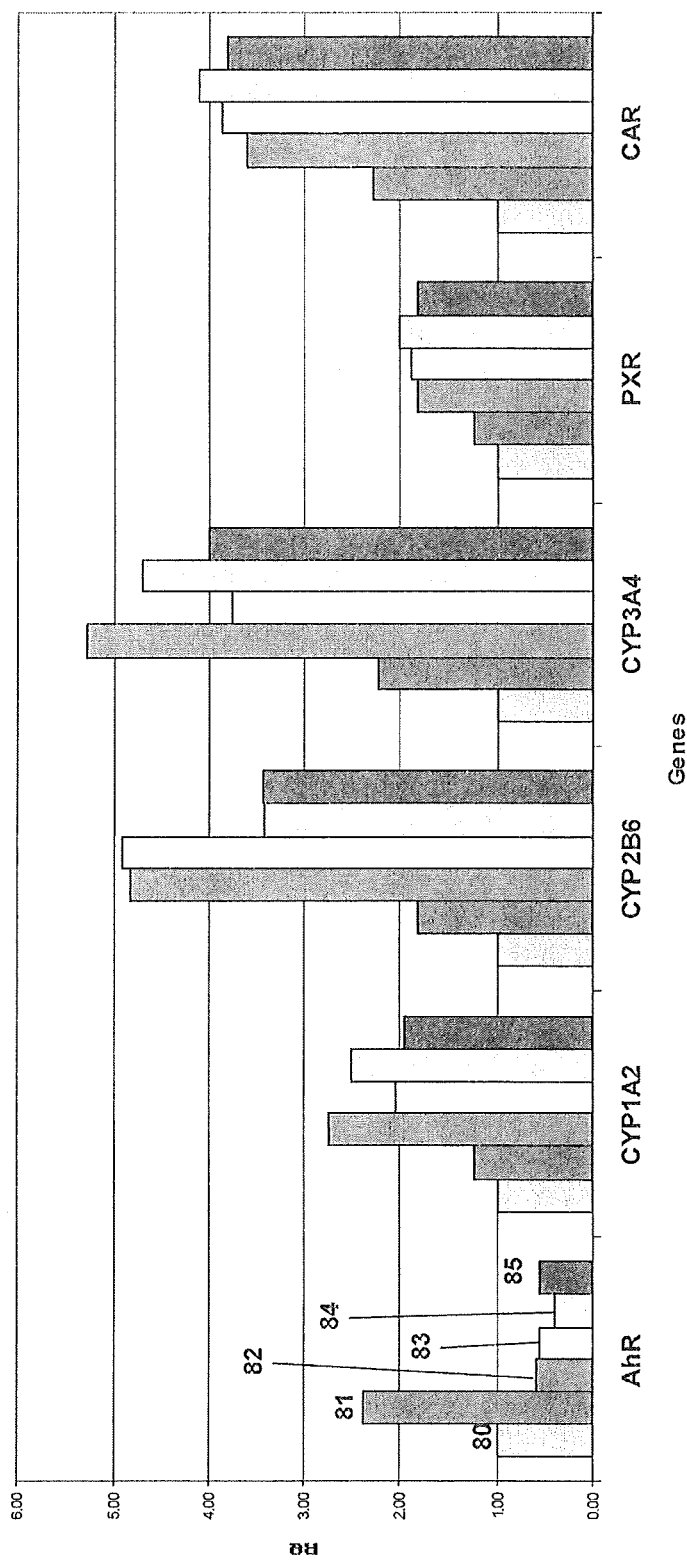
FIG. 5 shows a chart of relative quantitation for selected components present in and isolated from Matrigel as a cell culture coating and having a Matrigel (OL), and their comparative effect on gene expression.

FIG. 5 shows a chart of selected components present in or isolated from Matrigel as a cell culture coating and having a Matrigel (OL), and their comparative effect on gene expression. Here the doses studied apparently did not have much impact on gene expression. The reference numerals for each cluster of bars in the FIG. 5 chart represent, respectively: collagen-I only (80), Matrigel OL (81), BD laminin coating and Matrigel OL (82), laminin•entactin complex coating (1 microgram/cm$^2$) and Matrigel OL (83), laminin•entactin complex coating (5 microgram/cm$^2$) and Matrigel OL (84), and laminin•entactin complex coating (10 microgram/cm$^2$) and Matrigel OL (85).

Example 1

Simplified Matrix and Matrigel Component Overlay Analysis.

A first example examined the most abundant components of the Matrigel as overlays to determine the primary contributor(s), if any, for improved function as a result of overlay culture. This was accomplished by making a side-by-side overlay comparison of: Matrigel; the combination of the two major components of Matrigel (laminin•entactin complex and collagen-IV); the individual Matrigel components, and the combinations of the three individual (i.e., uncomplexed) components (laminin, entactin, and collagen-IV). The cellular morphology, the gene expression for general function, and CYP450 (a class of enzymes responsible for detoxification) were compared. The cells were cultured on a collagen type I coated surfaces and allowed to attach for 24 hours before the addition of the overlay. In this set of experiments, the overlays listed in Table 1 were compared.

TABLE 1

Comparison of Matrigel and selected Matrigel components as a cell culture overlay (OL).

| Overlay Component | Overlay Wt % (i.e., the concentration of component(s) added to the liquid media) | Wt. Ratio |
|---|---|---|
| No overlay (control) | — | — |
| Matrigel | 0.25 mg/mL | — |
| Laminin•Entactin Complex and Collagen-IV | 0.24 mg/mL, (95% in Matrigel, i.e., the percentage of lamin/ent/col IV in Matrigel) | 2.06 ratio (0.16 mg/mL vs. 0.0775 mg/mL) |
| Laminin•Entactin complex | 0.16 mg/mL (64% in Matrigel) | |
| Laminin | 0.14 mg/mL (56% in Matrigel) | — |
| Laminin and Collagen-IV mixture | 0.22 mg/mL, (87% in Matrigel) | 1.81 ratio (0.14 mg/mL vs. 0.0775 mg/mL) |
| Collagen-IV | 0.0775 mg/mL, (31% in Matrigel) | — |

From the gene expression experiments it was apparent that the laminin/entactin/collagen-IV overlay resulted in a similar gene expression profile to Matrigel. Unexpectedly, the laminin•entactin complex overlay alone had similar performance for the genes investigated. The laminin overlay alone, the collagen overlay alone, or an overlay combination of laminin and collagen-IV did not produce enhanced gene expression results. The entactin overlay alone also did not result in the enhanced gene expression profile. Hence, the data suggested that the laminin•entactin complex as a substrate coating or as an overlay appeared to be the major contributor in the enhancement in cell function. Other components in Matrigel could also contribute to the enhanced hepatic function found with Matrigel overlays, but the effects appear to be negligible or minor.

Example 2

Dose Response.

Since mouse entactin was not available commercially, recombinant human entactin was used to confirm whether both human and mouse entactin components were necessary in the 1:1 laminin and entactin complex, and to define the compositional ratio that has particularly useful performance. Furthermore, the dose response of the overlay concentration versus the cell function enhancement, as determined by gene expression and Multidrug Resistant Protein-2(MRP2) staining, was investigated.

According to the gene expression profile of selected genes, up to about 0.25 mg/mL of the laminin•entactin complex as an overlay appeared to provide an improvement in cellular function as the concentration of the laminin and entactin in the overlay was increased. Unexpectedly, however, the amount of entactin in the overlay showed an inversely proportional effect where lower amounts of entactin resulted in better cell function as measured by gene expression of certain genes, as shown in FIG. 3. However, in the absence of added laminin, the added entactin may have an inhibitory effect on cell binding. Entactin is a bridging molecule, for example, it bridges laminin and collagen, and its presence in higher concentration could result in binding of both macromolecules (laminin and collagen-IV or perlecan) without actually bridging them. The MRP2 staining results (images not shown) are consistent with the gene expression where the bile canalicular structure with the laminin and entactin complex overlay can be seen but not with either individual component, laminin or entactin, regardless of the concentration.

Example 3

Laminin and Entactin Complexation and Component Ratios.

To determine a laminin and entactin ratio for best (satisfactory to superior) cell function, mouse laminin and human recombinant entactin were mixed together, while keeping the entactin concentration constant and varying the laminin concentration. To reproduce a 1:1 complex, a laminin:entactin ratio of 7:1 (wt:wt) was required as a consequence of the mass difference between the two proteins. As shown in FIG. 4 a series of laminin and entactin mixtures were tested as an overlay (media additive) on human primary hepatocytes on collagen, in weight ratios of 7:1, 3.5:1, and 1.75:1 (laminin:entactin), in addition to a collagen control, a collagen with Matrigel overlay, and a laminin•entactin complex overlay. The laminin•entactin complex can be obtained by direct purification from Matrigel. A mixture of laminin and entactin can be made by mixing purified laminin with purified entactin at different ratios. Laminin and entactin form a specific, strong, 1:1 molar complex (i.e., the laminin•entactin complex). A purpose of mixing this complex with greater or lesser amounts of either entactin or laminin is to displace the 1:1 ratio to determine most advantageous ratios for cell culture.

The gene expression data presented in FIG. 4 for the selected gene panel (CYP genes and others) showed that the mouse laminin and human entactin complex did not enhance gene expression of the selected CYP450 enzymes or other genes tested. The physical mixtures of laminin and entactin components showed less gene expression than the laminin and entactin complex isolated from EHC sarcoma, possibly due to a shift in the compositional ratio as the laminin may still contain some entactin or a mismatch in species from which the components were derived. However, the MRP2 expression via immunochemical stains (images not shown) and fluorescent transport function showed an enhancement in bile duct formation and the ability of the cells to transport toxins into the bile ducts when the mixture of laminin and entactin was used as an overlay.

Example 4

The Laminin•Entactin Complex and Laminin Combinations for Cell Culture; Separate Combinations of Laminin•Entactin Complex and Laminin in Either Overlay and Substrate Coating.

Since the laminin•entactin complex as an overlay had a profound enhancement in cell function, the combination of having the substrate coated with the laminin•entactin complex (to more closely mimic in vivo culture where hepatocytes should see other cells or ECM) on all surfaces was explored. It is unlikely that a single cell would see only collagen on one side. To this end, a comparison was performed using Matrigel™ as an overlay and included substrates coated with (1) laminin (likely containing some entactin, since the laminin was isolated from laminin and entactin complex), and (2) laminin and entactin, and then compared with substrates coated with collagen-I (standard conditions). The gene expression data (data not provided) showed vast improvements in CYP450 expression and global function of human primary hepatocytes of cells cultured on laminin or the combined laminin and entactin coated substrates. Note that the laminin coated substrate may not be purified laminin and may contain entactin. This may account for the enhancement in performance relative to collagen-I. The use of a purified laminin (devoid of any entactin) coating did not produce cells with similar level of gene expression as was verified experimentally.

In addition, the MRP2 staining shows more extensive bile canalicular structure for hepatocytes cultured with laminin and entactin coating with Matrigel™ overlay than cells cultured on collagen with or without a Matrigel overlay. Hence, although the cells were not in spheroid clusters as they would appear on Matrigel™ (thick gel), their gene expression profile, and extensive canalicular network formation more closely resembles that of a 3D culture, such as a cluster (spheroid) without the challenges associated with culturing cells in 3D (such as imaging, diffusion, cell harvesting, and compatibility with automated high content screening (HCS). The cells adopt a more cord-like network in a somewhat uniform monolayer in culture. Replacing the Matrigel™ overlay with a laminin and entactin overlay on hepatocytes cultured on a laminin and entactin coating or a laminin only coating yields a laminin and entactin sandwich which can further enhance the function of the cells and further extends the formation of the bile canaliculi network.

Example 5

Accessibility of Laminin and Entactin (AFM)—May Cause a Conformation or Accessibility Change.

Entactin is a small protein and is partially hidden by its binding to laminin. However, the large differences observed in cellular function prompted exploration of the accessibility of entactin vs. laminin and their topographical (polymerization) differences. The binding event of laminin to entactin could presumably cause a conformational change and alter the crosslinking properties of the resulting biopolymer. Although not limited by theory, the differences in cellular function may be attributed to specific interactions. The topographical differences and accessibility of the same or similar peptide sequences may be changed as a consequence of conformational change.

Using atomic force microscope (AFM) pulling experiments, the AFM tip was used to probe nonspecific interactions between the cantilever and the proteins bound to the substrate. Pulling at proteins on the surface gave a relative indication of protein size and indications of protein accessibility. The tip of the AFM cantilever interacts with a protein on the substrate where binding events could take place. Lifting the cantilever causes unfolding of the protein and the distance the protein could be pulled before the temporary binding snap back. The resulting consistent saw tooth patterns (graphical data presentation not shown) permit differentiation between different proteins and also detection of conformational differences within the same protein, such as accessibility to different domains within the same protein. The laminin only sample produced about 210 pulls per 1024 attempts whereas the laminin•entactin complex sample produced about 395 pulls per 1024 attempts. The nominal stiffness was 0.01 N/m.

Laminin•entactin complex is similar in size to laminin itself. The laminin•entactin complex is 7:1 weight ratio which is 1:1 molar ratio as laminin•entactin forms a 1:1 complex.

Pure laminin had half the number of adhesion events with the AFM cantilever and longer pulls. Laminin•entactin complex had twice the number of adhesion events (with cantilever), having shorter and longer pulls. This suggests that entactin may be accessible by a probe, or a different orientation that makes another previously inaccessible domain of laminin accessible. The pulls are significantly different in contour length.

Example 6

Laminin•Entactin Complex Formulation.

Mouse laminin•entactin complex (cat. no. 354259) and ultrapure mouse laminin (cat. no. 354239) were obtained from Becton-Dickinson Biosciences. Recombinant human entactin was obtained from R&D systems (cat. no. 2570-ND).

Example 7

Laminin•Entactin Complex Substrate Coating.

The commercially available mouse laminin•entactin complex was thawed slowly at 4° C. over about 16 hours. The coating procedure was performed over ice. The stock solution (10.8 mg/mL) was diluted in pre-chilled serum-free MFE media to obtain three working solutions at concentrations of 100 micrograms/mL, 50 micrograms/mL, and 10 micrograms/mL, respectively. The working solutions were then placed into respective wells to the final concentration to surface area of 1, 5, and 10 micrograms/cm$^2$. For example, adding 33 microliters of each working solution per well of 96-well plate to reach the final concentration to surface area of 10, 5, and 1 micrograms/cm$^2$. The coated plate was incubated at 37° C. for one hour and then washed once with serum-free media before use.

Example 8

Laminin Substrate Coating.

The commercially available ultrapure mouse laminin was thawed at 4° C. over about 16 hours. The coating procedure was performed over ice. The stock solution (2 mg/mL) was diluted in to pre-chilled serum-free MFE media to make a working solution with the concentration of 100 micrograms/mL. The working solution was then placed into each well to the final concentration of 10 micrograms/cm$^2$ surface area, as mentioned above. The coated plate was incubated at 37° C. for one hour and then washed once with serum-free media before use.

Example 9

Laminin•Entactin Complex Overlay Deposition.

Matrigel is composed of about 56% of laminin, about 31% of collagen-IV, about 64% of laminin•entactin complex, and about 8% entactin. The dose of laminin•entactin complex overlay was used at either the same percentage of the components in Matrigel or the same weight dose of Matrigel overlay. When using the percentage of Matrigel, 0.16 mg/mL of laminin•entactin complex working solution was diluted from the BD laminin•entactin complex stock solution (10.8 mg/mL) in pre-chilled MFE media. When using the same weight of Matrigel, the BD laminin•entactin complex stock was diluted to 0.25 mg/mL in pre-cold MFE media. In the study on the molecular mass ratio of laminin to entactin the ratio based on the weight dose of Matrigel was calculated, i.e., the final concentration for the overlay was 0.25 mg/mL. Laminin (MW about 810 kDa) stock and recombinant entactin (MW about 130 kDa), were calculated using molecular weight at a weight ratio of 7:1, 3.5:1, 1.75:1, and 1:1, and diluted in pre-chilled MFE media to make the mixtures. All of mixtures were prepared over ice and adjusted pH to 7.4-7.5 before being added to the cultures, such as placing 100 microL/well in a 96-well plate.

Example 10

Laminin Overlay Deposition.

Matrigel is composed of about 56% of laminin. The dose of laminin overlay was used at either 56% of the Matrigel overlay dose or the same dose weight of a Matrigel overlay. When using the percentage of Matrigel, 0.14 mg/mL of laminin working solution was diluted from BD laminin stock (2 mg/mL) in pre-chilled MFE media. When using the same weight dose of Matrigel, the BD laminin stock was diluted to 0.25 mg/mL in pre-chilled MFE media. Both mixtures were prepared over ice and the adjusted pH to 7.4-7.5 before being added to the cultures, such as placing 100 microL/well in a 96-well plate.

Experimental

Cell Culture.

Cryo-preserved primary hepatocytes (Lot 770, XenoTech, LLC) were thawed and plated at 60K per well of 96-well plates with serum-free Multifunctional Enhancement (MFE™) plating media. An alternative media can be, for example, Williams Medium E. The cells were allowed to attach overnight. The overlay of Matrigel and extracellular matrix (ECM) components were performed on the second day during media change. The cells were maintained in MFE maintenance media for seven days. The qPCR analysis was performed on day seven of the culture.

Matrigel overlay: Matrigel removed from a Becton Dickinson (BD's) E-well Matrigel Biocoat plate was diluted in pre-chilled MFE media to 0.25 mg/mL and added to the culture of a 96-well plate at 100 microL per well.

In the ECM study each ECM component was used by the percentage of Matrigel, i.e., 56% of laminin, 31% of collagen-IV, 64% of laminin•entactin complex, and 8% of entactin. The dose of each component was calculated based on the routine dose of Matrigel overlay (0.25 mg/mL). All of these ECM mixtures were prepared by diluting in MFE media, kept over ice, and the pH adjusted to 7.4-7.5 before being added to the cultures at 100 microL/well.

Collagen-I plates were purchased from BD, cat. no. 354407. All BD Biocoated plates were on tissue-culture treated (TCT) clear polystyrene. The concentration of ECM was unspecified.

Protein Coating for AFM Experiments.

Murine sourced (EHS sarcoma) laminin (from BD & Company, 2 mg/mL, cat. no. 354239) was slowly thawed from −40° C. to −4° C. over 16 hours. The laminin solution and pre-chilled PBS (4° C.) was chilled by inserting the vials in crushed ice to keep the PBS and laminin at 0° C. for the dilution process. 0.025 mL of the 2 mg/mL laminin was added to 0.975 mL PBS in an Eppendorf tube and mixed by inverting the tube three times to dilute to 0.50 micrograms laminin/mL. The diluted laminin was added to a pre-chilled 60 mm TCT polystyrene dish where a 15 mm circle was drawn on the bottom of the plate, and the solution was carefully spread without touching the pipette tip to the dish in the confines of the 15 mm boundary. The dish was incubated (1 hr, RT) in a humidity chamber with the lid on to prevent evaporation during the incubation step. The solution was again carefully removed taking care not to touch the plate with the pipette tip and washed 3× with chilled PBS. The dish was then filled with 4 mL PBS and kept under PBS for the remainder of the experiment.

Laminin and entactin (BD 10.8 mg/mL, cat. no. 354259) was slowly thawed from −40° C. to −4° C. (over 6 hours). The laminin and entactin solution as well as pre-chilled PBS (4° C.) was kept cold by inserting the vials in crushed ice to keep the PBS and laminin at 0° C. for the dilution process. The solution was first diluted to 1 mg/mL by adding 93 microL of laminin and entactin (7:1=wt.:wt.) to 907 microL PBS. The stock solution was then diluted by adding 50 microL of the 1 mg/mL laminin and entactin solution to 950 microL of pre-chilled PBS to get a 50 micrograms/mL coating solution. The diluted solution was added to a pre-chilled 60 mm TCT polystyrene dish where a 15 mm circle was drawn on the bottom of the plate, and the solution was carefully spread without touching the pipette tip to the dish in the confines of the 15 mm boundary. The dish was incubated (1 hr, RT) in a humidity chamber with the lid on to prevent evaporation during the incubation step. The solution was again carefully removed taking care not to touch the plate with the pipette tip and washed three times with chilled PBS. The dish was then filled with 4 mL PBS and kept under PBS for the remainder of the experiment.

Table 2 shows actual and comparative image analysis results for several cell culture systems.

TABLE 2

| Cell Culture System and Composition (substrate coating, overlay, or both) | Image characterization and visual analysis of MRP2 immunostaining (indicating bile canalicular structure) |
|---|---|
| Collagen-I coating without overlay | Bile canalicular structures show dot shape |
| Collagen-I coating with Matrigel overlay | Bile canalicular structures show extended branch shape |
| Collagen-I coating with laminin•entactin complex overlay | Similar to Matrigel overlay |
| Collagen-I coating with laminin only overlay | Bile canalicular structures show mixed long shape or dot shape |
| Collagen-I coating with entactin only overlay | Bile canalicular structures show dot shape structures with significant reduced cell numbers |
| Collagen-I coating with laminin and entactin mixture (7:1 ratio) overlay | Similar to Matrigel overlay |

The gene types used for expression evaluation include: Aryl hydrocarbon receptor (AhR); Cytochrome P4501A2 (CYP1A2); Cytochrome P4501A2 (CYP2B6); Cytochrome P4501A2 (CYP3A4); Pregnane X receptor (PXR); and Constitutive androstane receptor (CAR).

Table 3 summarizes combinations of surface coating and overlay (OL) and their respective gene expression cell culture performance.

TABLE 3

| Coating | Overlay (OL) | Performance |
|---|---|---|
| Collagen-I | not applicable | − |
| Fibronectin | not applicable | − |
| Laminin | not applicable | − |
| L•E | not applicable | − |
| Collagen-I | Matrigel | +/− |
| Fibronectin | Matrigel | +/− |
| Laminin | Matrigel | +/− |
| L•E | Matrigel | +/− |
| Collagen-I | L•E | +/− |
| Matrigel | L•E | + |
| Laminin | L•E | + |
| L•E | L•E | +/− |
| L•E | Laminin | | i. +/− comparable or nearly identical to Matrigel OL with collagen coating
ii. + improved gene expression performance comparable to collagen coating only
iii. L•E is the laminin•entactin complex

AFM.

A Veeco Bioscope II scanning probe microscope (with Nanoscope V Controller), in contact mode, was used to perform force spectroscopy on the coatings. MSCT and OBL cantilevers were used as supplied by the manufacturer, without specific functionalization, to allow for the widest range of random protein adsorption in the initial measurements. Analysis of the spectroscopic profiles is based on accurate z-scale piezo calibration (within 3% of NIST-traceable standard 821/1261555-99 180QC/3421-17-23).

Data was generally acquired on a 32×32 grid over a 10 microns×10 microns region of the sample (1024 unfolding attempts per region). Force spectroscopy allows for indirect probing of the conformation of proteins attached or adsorbed to a substrate. If proteins adsorb onto the AFM probe, separating the cantilever from the substrate may forcibly unfold the polymers. Successful pulling attempts can be presented in the force curves profiles (deflection vs. extension)(data not shown). The saw-tooth force signatures, which result from protein-tip bond rupture, can be fitted to models such as the Wormlike Chain, to extract lower-limit estimates of the contour length and molecular weight of the domains being unfolded. In the Wormlike Chain Model, the force F required to stretch a folded polymer to extended length x is:

$$F(x) = \frac{k_B T}{4p}\left[\left(1-\frac{x}{L}\right)^{-2} + \frac{x}{L} - \frac{1}{4}\right], \quad b.$$

where $k_B$ is Boltzmann's constant, T is temperature, p is the persistence length, and L is the contour length of the protein polymer. Since it is unclear if a single force profile represents the extension of one or several polymers simultaneously, meaning cannot be attributed to the extracted persistence lengths, which vary with the number of polymers being simultaneously unfolded. However, physical meaning can be drawn from the contour length, which is the length of the fully extended polymer domain being stretched and serves as a lower limit for the linear dimensions of the whole protein or of the domain being unfolded. It is generally believed that the extension of each domain in a protein corresponds to a saw-tooth shape in the force curve, as described by the functional form above. Fits can be performed on force curve data to extract contour lengths, but a reasonable estimate can be obtained by taking the extension at which the cantilever snaps back to the horizontal axis, forming the saw-tooth shape.

The disclosure has been described with reference to various specific embodiments and techniques. However, it should be understood that many variations and modifications are possible while remaining within the scope of the disclosure.

What is claimed is:

1. A cell culture system comprising:
   a substrate;
   a coating on the substrate;
   one or more live cells on the coated substrate; and
   an overlay layer atop the live cells, the substrate coating consists of an isolated and purified, laminin, and the overlay layer consists of an isolated and purified, laminin and entactin complex having the laminin and the entactin associated in a mole ratio of 1:1, and the live cells are selected from hepatocytes, primary hepatocytes, mammalian hepatic cell lines, stem cells, or combinations thereof.

2. The system of claim 1 further comprising a liquid media, a cover, and combinations thereof.

3. The system of claim 2 wherein the liquid media further comprises an overlay source comprising an isolated and purified, laminin and entactin complex and serum free media, and the cover comprises a removable gas permeable, liquid leak-proof seal.

4. The system of claim 1 wherein the laminin is murine sourced and the entactin is human sourced.

5. The system of claim 1 wherein the isolated and purified laminin and entactin complex consists of the laminin and the entactin in a relative weight ratio of about 5:1 to about 9:1.

6. The system of claim 1 wherein the isolated and purified laminin is present in the substrate coating in an amount of from about 1 microgram/cm$^2$ to 20 microgram/cm$^2$, and the isolated and purified laminin and entactin complex is present in the overlay in an amount of from about 0.25 milligrams/mL to about 1 milligrams/mL.

7. The system of claim 1 wherein the isolated and purified, laminin and entactin complex and the laminin are each essentially free of endogenous growth stimulants, proteolytic enzymes, or combinations thereof.

8. The system of claim 1 wherein the substrate comprises a petri dish, a cell culture flask, a multi-well plate, a non-porous slide, a porous slide, a chamber/multi-chamber slide, a cell culture device, a microcarrier, or combinations thereof.

9. A method of making a cell culture article comprising:
   laminin coating a substrate, the laminin coating consisting of an isolated and purified laminin;
   contacting the laminin coated substrate with live cells to form at least a monolayer of the live cells on the coated laminin substrate;
   providing an overlay source consisting of an isolated and purified laminin and entactin complex to form an isolated and purified laminin and entactin complex overlay on the live cells on the coated substrate.

10. The method of claim 9 further comprising removing the overlay source from the article.

11. The method of claim 10 further comprising adding a liquid media to the article.

12. A method of culturing cells comprising:
    providing the cell culture system of claim 1; and
    providing a user selected media to the article.

13. The method of claim 12 wherein the user selected media is serum free.

14. A cell culture article comprising:
    a substrate;
    an isolated and purified, laminin layer on the substrate;
    a live cell layer on the isolated and purified, laminin layer; and
    an isolated and purified, laminin and entactin complex overlay layer on the cell layer, and the live cells of the live cell layer are selected from hepatocytes, primary hepatocytes, mammalian hepatic cell lines, stem cells, or combinations thereof.

15. The system of claim 1 wherein the laminin, the entactin, or both, are selected from a murine source, a human source, or both a murine source and a human source.

16. The system of claim 1 wherein the live cells of the live cell layer are primary hepatocytes.

17. The article of claim 14 wherein the live cells of the live cell layer are primary hepatocytes.

* * * * *